United States Patent
Gadrat et al.

(10) Patent No.: US 8,905,960 B2
(45) Date of Patent: Dec. 9, 2014

(54) DEVICE FOR THE FILTERING A COMPLEX LIQUID SUCH AS BLOOD, IN PARTICULARLY APPLICABLE TO AN AUTOTRANSFUSER

(75) Inventors: Francis Gadrat, Bordeaux (FR); Bertrand Chastenet, Eysines (FR)

(73) Assignee: Direction et Priorites, Gradignan (FR)

( * ) Notice: Subject to any disclaimer, the term of this patent is extended or adjusted under 35 U.S.C. 154(b) by 0 days.

(21) Appl. No.: 12/991,794

(22) PCT Filed: May 14, 2009

(86) PCT No.: PCT/FR2009/050903
§ 371 (c)(1),
(2), (4) Date: Nov. 9, 2010

(87) PCT Pub. No.: WO2009/147356
PCT Pub. Date: Dec. 10, 2009

(65) Prior Publication Data
US 2011/0058983 A1   Mar. 10, 2011

(30) Foreign Application Priority Data
May 14, 2008   (FR) ..................... 08 53112

(51) Int. Cl.
*A61M 1/02* (2006.01)
*A61M 1/36* (2006.01)
(Continued)

(52) U.S. Cl.
CPC ..... *A61M 1/3633* (2013.01); *A61M 2005/1657* (2013.01); *B01D 29/01* (2013.01);
(Continued)

(58) Field of Classification Search
CPC .. A61M 1/34; A61M 1/3496; B01D 2029/01; B01D 23/02; B01D 23/08; B01D 2321/2016; B01D 29/01; B01D 29/41; B01D 61/18; B01D 61/20; B01D 63/08; B01D 63/087; B01D 65/08

USPC ........... 604/4.01, 5.01, 5.04, 6.01, 6.03, 6.09, 604/406; 210/645, 433.1, 274, 649, 650, 210/651, 321.65, 411, 194, 321.75, 321.84, 210/512.1, 767, 805
See application file for complete search history.

(56) References Cited

U.S. PATENT DOCUMENTS 3,556,302 A * 1/1971 Agranat .................. 210/321.84
4,375,415 A * 3/1983 Lavender ..................... 210/651
(Continued)

FOREIGN PATENT DOCUMENTS

DE   9104912 U1   9/1991
FR   2371954 A1   6/1978
(Continued)

OTHER PUBLICATIONS

International Search Report, dated Dec. 10, 2009, from corresponding PCT application.

*Primary Examiner* — Adam Marcetich
(74) *Attorney, Agent, or Firm* — Young & Thompson

(57) ABSTRACT

A device for the filtration of a complex fluid composition such as blood, includes a base (12) with a bottom (18), a top (14) with a bottom (30), and a membrane (16) that is arranged between the base and the top so as to define a low chamber C1 and a high chamber C2, with an input tap (26) of the complex composition that is to be filtered emptying into the low chamber C1, an output tap (28) of the retentate with elements for adjusting the flow rate emptying into this same low chamber C1, and an output tap (36, 36-1) of the high chamber C2, whereby this output tap (36, 36-1) of the permeate is subjected to negative pressure.

14 Claims, 2 Drawing Sheets

(51) Int. Cl.
   *B01D 29/01* (2006.01)
   *B01D 65/08* (2006.01)
   *B01D 29/00* (2006.01)
   *B01D 29/41* (2006.01)
   *B01D 61/20* (2006.01)
   *B01D 61/18* (2006.01)
   *B01D 63/08* (2006.01)
   *A61M 1/34* (2006.01)
   *A61M 5/165* (2006.01)

(52) U.S. Cl.
   CPC ............... *A61M 5/165* (2013.01); *B01D 65/08* (2013.01); *B01D 23/08* (2013.01); *B01D 29/41* (2013.01); *A61M 2202/0042* (2013.01); *A61M 2205/7563* (2013.01); *B01D 61/20* (2013.01); *A61M 2206/12* (2013.01); *B01D 61/18* (2013.01); *A61M 2202/0035* (2013.01); *B01D 63/087* (2013.01); *B01D 2313/086* (2013.01); *A61M 1/3417* (2013.01)
   USPC ....... 604/6.09; 604/6.01; 604/6.11; 604/6.15; 210/194; 210/321.75; 210/321.84; 210/433.1; 210/512.1; 210/650; 210/767; 210/805

(56) References Cited

U.S. PATENT DOCUMENTS

| | | | |
|---|---|---|---|
| 4,411,792 | A | 10/1983 | Babb |
| RE32,089 | E * | 3/1986 | Blatt et al. ..................... 210/651 |
| 4,780,202 | A * | 10/1988 | Kaartinen et al. ............ 210/247 |
| 4,846,970 | A * | 7/1989 | Bertelsen et al. ............ 210/232 |
| 4,861,476 | A * | 8/1989 | Kohlheb et al. .......... 210/321.76 |
| 4,935,002 | A | 6/1990 | Gordon |
| 5,141,639 | A * | 8/1992 | Kraus et al. .............. 210/321.75 |
| 5,183,569 | A * | 2/1993 | Kyriacou ....................... 210/636 |
| 5,601,727 | A * | 2/1997 | Bormann et al. .............. 210/767 |
| 5,616,254 | A * | 4/1997 | Pall et al. ....................... 210/806 |
| 5,762,789 | A * | 6/1998 | de los Reyes et al. ... 210/321.75 |
| 5,919,330 | A * | 7/1999 | Pall et al. ....................... 156/305 |
| 6,508,859 | B1 * | 1/2003 | Zia et al. ........................... 95/46 |
| 6,660,171 | B2 * | 12/2003 | Zuk, Jr. ......................... 210/767 |
| 6,926,834 | B2 * | 8/2005 | Coville et al. ................. 210/650 |
| 2005/0189297 | A1 * | 9/2005 | Bosch et al. ................... 210/651 |
| 2006/0043021 | A1 * | 3/2006 | Pesakovich et al. .......... 210/650 |
| 2006/0060084 | A1 * | 3/2006 | Edlund et al. ....................... 96/4 |
| 2010/0044310 | A1 * | 2/2010 | Wan et al. ..................... 210/637 |

FOREIGN PATENT DOCUMENTS

| FR | 2554010 | A1 | 5/1985 |
|---|---|---|---|
| FR | 2874327 | A1 | 2/2006 |
| JP | 02095421 | A | 4/1990 |

* cited by examiner

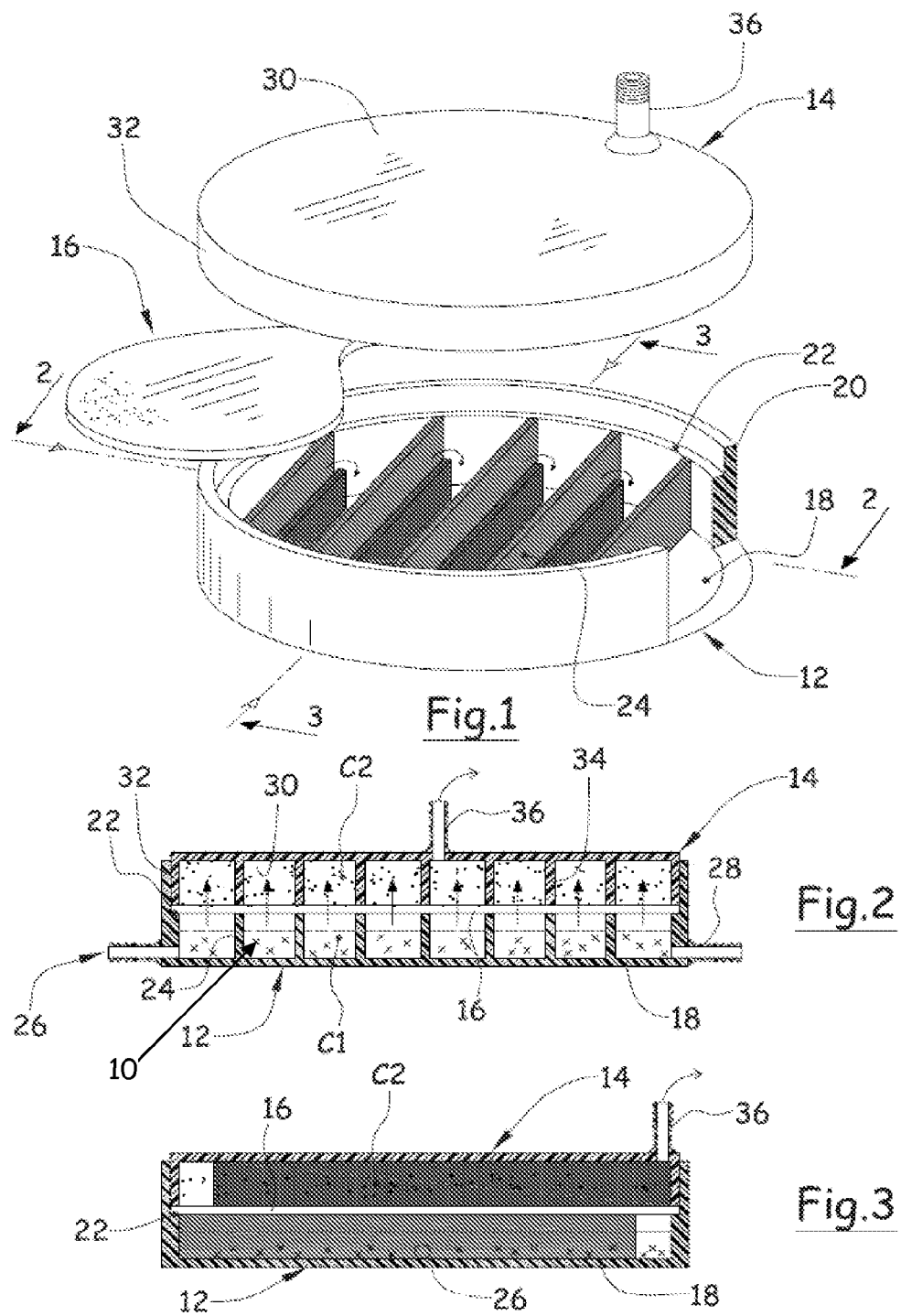

DEVICE FOR THE FILTERING A COMPLEX LIQUID SUCH AS BLOOD, IN PARTICULARLY APPLICABLE TO AN AUTOTRANSFUSER

BACKGROUND OF THE INVENTION

1. Field of the Invention

This invention relates to a device for the filtration of a complex liquid such as blood, in particular able to be integrated in a device for processing blood for the purpose of an autotransfusion.

2. Description of the Related Art

It is known that the filtration of blood so as to remove impurities or certain compounds in particular in the case of an autotransfusion poses numerous problems, in particular the clogging of filtering surfaces.

The pores of these filtering surfaces are modified as the filtration conditions proceed, although the filtration flow rate decreases until it becomes zero.

Hereinafter, the example that is adopted is blood, which is a heterogeneous medium, the filtration device according to this invention being applied for any liquid composition that has identical problems. Thus, the presence of proteins of more or less significant molecular weights as well as cellular elements is found in the blood. If a filtration threshold is provided to eliminate them, these protein chains and cellular elements will block the pores of the filtration surface preventing the passage of elements to be filtered, and even water.

It is also noted that the permeation in the existing membranes occurs perpendicular to the surface, whereby the liquid volume that is to be filtered is placed above the membrane, and the filtrate is below. Placing under vacuum also makes it possible to promote the passage unless clogging occurs, because then the negative pressure promotes the plating of the clogging layer and on the contrary emphasizes this phenomenon.

This phenomenon can also be aggravated by the deposition of certain elements that compose the liquid phase that is to be filtered. In this case, gravity has a tendency to make these elements accumulate on the filtering surface, accelerating the clogging phenomenon, all the more if there is negative pressure. One solution would consist in stirring the composition that is to be filtered, but this is not easy to achieve if simple systems are sought.

If it is desired, for example, to integrate such a filtration device, for example in an autotransfuser such as the one that is described in French Patent Application No. 2,874,327, such stirring means are not conceivable.

BRIEF SUMMARY OF THE INVENTION

It is suitable to propose an arrangement that allows a filtration of a quantity of complex liquid composition with a flow rate that decreases only slightly over time, which remains very compact to allow integration in, for example, an autonomous autotransfusion device, which is a small price for being able to apply to the largest number, which uses existing filtration membranes so as to prevent the development of specific membranes, and which can be accepted by the medical authorities.

This is the purpose of the filtration device according to this invention.

BRIEF DESCRIPTION OF THE DRAWINGS

The filtration device is now described in detail according to a particular, nonlimiting embodiment relative to the accompanying drawings in which the various figures show:

FIG. 1: A diagrammatic perspective view of the device according to the invention, FIG. 2: A vertical transverse cutaway view along line 2-2 of FIG. 1, FIG. 3: A vertical transverse cutaway view along line 3-3 of FIG. 1, FIG. 4: A diagrammatic view of an installation that is equipped with a device according to this invention.

DETAILED DESCRIPTION OF THE PREFERRED EMBODIMENTS

Figure 4:
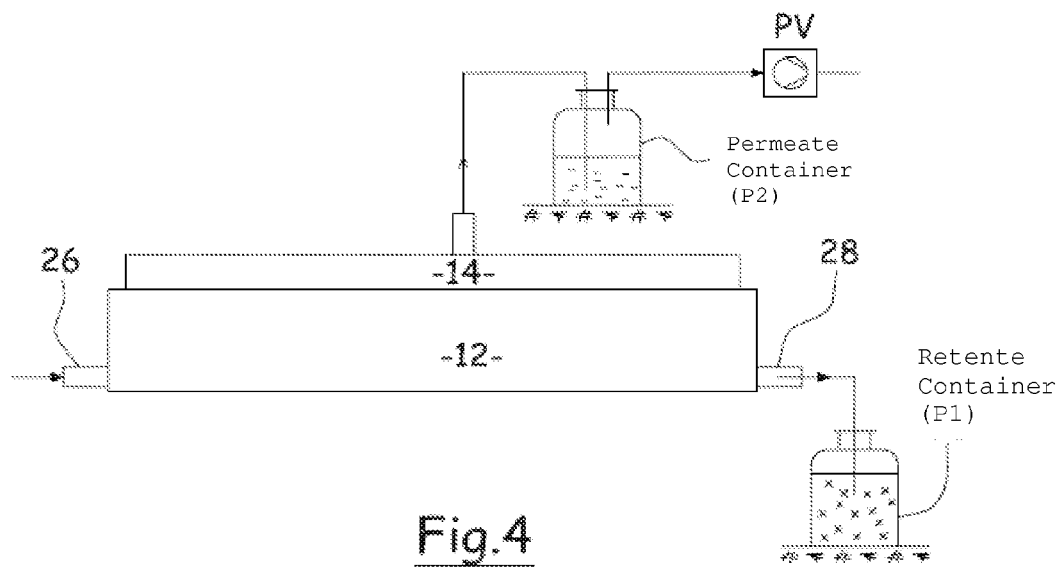

FIG. 1 shows a device for the filtration of a complex liquid 10, whereby said device comprises a base 12 and a top 14 that can be interlocked in said base.

The different elements are advantageously made of plastic material that can be molded with precision and that has a medical and/or alimentary compatibility according to the applications in question. In this case for an application to the filtration of blood, in particular for the purpose of an autotransfusion, the plastic material uses all of the necessary capabilities to meet the standards involved.

The base 12 and the top 14 therefore emerged from molding with a precision such that the interlocking with gentle friction ensures sealing when the two parts are totally interlocked, as will be explained below.

A filtration membrane 16 is inserted between the base 12 and the top 14. This membrane 16 has a cutoff threshold that is adapted to the product to be filtered as will be explained further in the description.

The base 12 is of the cylindrical type with a bottom 18 and an annular wall 20.

This annular wall 20 comprises a flange 22 that defines a first inside diameter d and a second inside diameter D. The second diameter D corresponds to the outside diameter of the top 14, aside from the airtight interlocking.

The bottom 18 comprises ribs 24 that have come from molding with said bottom. These ribs have a height such that they come to the right of the flange 22. These ribs 24 form baffles that alternately come from the circular wall 20 via one of their ends without reaching this same circular wall 20 at the other end.

The base 12 comprises an input tap 26 whose direction for introducing the fluid is oriented perpendicular to the plane of the ribs 24.

The input tap 26 is implanted below the flange 22 to empty into the low chamber C1, defined by the membrane 16, the bottom 18 of the base 12, and the annular wall 20 of this very base.

The base 12 also comprises an output tap 28, arranged diametrically opposite to the input tap 26.

The output tap 28 is implanted below the flange 22 to exit from the low chamber C1, defined by the membrane 16, the bottom 18 of the base 12, and the annular wall 20 of this same base.

The top 14 comprises a bottom 30 and an annular wall 32.

The annular wall 32 has a thickness that is essentially equal to the width of the flange 22 of the base 12.

The membrane 16 is thus at least immobilized peripherally between the flange 22 of the base 12 and the annular wall 32 of the top 14, as can be seen in FIGS. 2 and 3.

The top 14 is equipped with ribs 34, obtained from molding with the bottom. These ribs are also obtained from molding by one end of the annular wall 32, without reaching this same annular wall 32 via the other end. These ribs 34 therefore form a set of baffles that is equivalent to that of the baffles 24 of the base 12.

The baffles 24 of the base 12 and the ribs 34 of the top are opposite so as to immobilize the membrane 16. One skilled in the art will adjust the heights of the ribs to ensure a suitable tightening after assembly based on the thickness of said membrane in particular but also its nature.

An output tap 36 is located in the bottom 30 of this top.

A second high chamber C2 is defined by the membrane 16, the bottom 30, and the annular wall 32.

It is noted that the membrane 16 is not only held by its periphery but also between the ribs 24 of the base 12 and the ribs 34 of the top 14.

Thus, the membrane is held perfectly.

Advantageously, it is possible to provide a groove on the flange 22 of the base 12 and a tab profile that matches that of the groove, so as to further improve the immobilization, on the section of the annular wall 32 of the top. This improvement is only one of the means of improving the tightening, with any other equivalent means being included in this application.

The device according to this invention is implemented in the following way.

According to the applications, the modules are made with the membrane 16 that has the desired cutoff threshold.

Each device is advantageously made in a factory under conditions that are suitable for medical equipment when this is its purpose.

The two parts, base 12 and top 14, are interlocked after the membrane 16 has been arranged.

Advantageously, a peripheral welding by ultrasound or laser makes it possible to weld the two plastic parts and ensures total sealing.

This very precise and localized peripheral welding creates only an insignificant heat input and does not cause any degradation of the membrane itself.

In referring to FIG. 4 in addition to the first three figures, the operator connects the tap 26 to the supply of the composition that is to be purified, for example a blood composition that is obtained from a drain following a surgical intervention.

The output tap 28 of the base 12 is connected to a container P1 that is provided for collecting the retentate, i.e., the elements that are held by the filter.

The tap 36 of the top is connected to a container P2 that is provided for collecting the filtrate that is to be eliminated. This container P2 is advantageously put under negative pressure by connection to a vacuum source PV.

The output tap 36 of the high chamber C2 is therefore subjected to negative pressure if necessary.

The composition is introduced into the low chamber C1 and circulates in the set of baffles of the ribs 24.

The output tap 28 comprises means for adjusting the flow rate so as to create a slight pressure in the chamber C1 of the filter if the flow rate is reduced a little.

It is necessary to take into consideration the loss of the volume of permeate passed through the membrane that reduces the flow rate through the tap 28 and the loss of transmembrane pressure.

Because of this slowed circulation, a deposition of the heaviest particles also occurs. In addition, the circulation through the baffles creates a separation that holds the heaviest particles in the core of the flow or in the low part while the fluid that is slightly charged remains on the surface.

In parallel, the composition circulates against the membrane and under the effect of different parameters, balancing of flow rates and of slight negative pressure; the bulk of the small particles and the fluids pass tangentially to the membrane 16 and pass through it to arrive in the chamber C2 while the large particles on the cutoff threshold remain in the chamber C1, and this charged fluid exits via the output tap 28 of the base 12.

This permeation extends throughout the circulation of the composition in the chamber C1 although one particle that is not immediately drawn in through the membrane 16 when it could be will be potentially drawn in through the peregrination of said composition along the membrane 16. It is noted that the deposited particles of suitable sizes pass through the membrane and cannot clog said membrane, which is particularly advantageous.

As for other particles that are too large to pass through the membrane, they do not accumulate against the wall of the membrane because of the tangential circulation and gravity, therefore very greatly limiting the clogging and the reduction of the permeation flow rate.

It is important not to generate too significant a negative pressure and too fast a flow rate because the particles would be plated against the membrane as in the arrangements of the prior art.

The entire surface of the membrane is stressed, greatly improving the yield for a given filtration surface.

As a result, this type of filtration device can have a reduced space requirement for a filtration capacity that is equivalent to that of a filter of the prior art.

Figure 5:
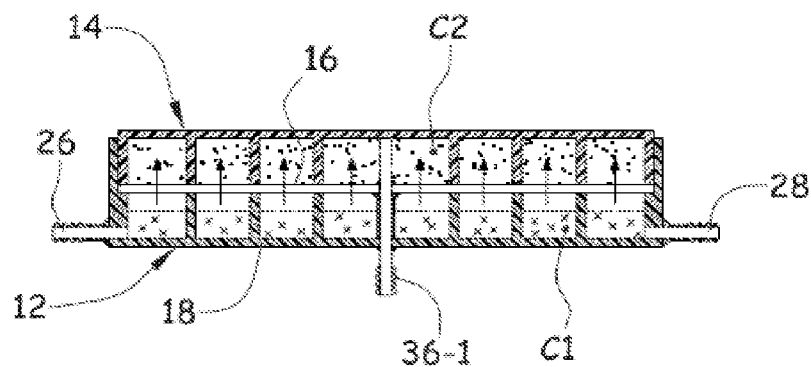
FIG. 5: A cutaway view of an arrangement that is suitable in particular for being combined with an autotransfuser.

FIG. 5 shows an embodiment with a tap 36-1, reversed, whereby the other elements are identical.

In an airtight way, this tap 36-1 passes through the bottom 18 of the base 12 and comprises perforations in its part that is located within the high chamber C2. The membrane 16 is also perforated to allow this tap 36-1 to pass, with the membrane being adjusted in an airtight manner around said tap 36-1.

Such an arrangement makes possible an easy integration into an autotransfusion device such as the one of the French Patent Application No. 2 874 327.

In the same manner, the concentrated fraction or retentate will be withdrawn at the outlet by the output tap 28 while the permeate will be withdrawn by the tap 36-1.

Such a filtration device with a complex composition is very advantageous in terms of manufacturing, also using only known techniques, and the filtrating membrane does not need to be special if this is not in terms of dimensions, which is not a problem. The existing membranes have an entirely adequate mechanical strength, taking into account the fact that it is perfectly supported by the ribs and by the periphery.

It is also noted that because of the non-clogging of the filter, the flow rate varies very little, and the processing time of the complex composition is quick.

The invention claimed is:

1. A device for the filtration of a complex fluid composition, comprising:
    a base with a bottom extending in a first direction;
    a top arranged over the base;
    a first side extending between the base and the top;
    a second side opposite the first side extending between the base and the top;
    a membrane that is arranged between said base and said top so as to define a low chamber and a high chamber, the first and second sides being disposed with the low and high chambers therebetween;
    an input tap of the complex fluid composition to be filtered that empties into the low chamber through the first side, the low chamber being disposed below the high chamber with respect to a direction of flow of the complex fluid composition from the low chamber to the high chamber, the direction of flow from the low chamber to the high chamber being transverse to the first direction and opposite a direction of gravity so that gravity assists in limiting the clogging of the membrane with particles too large to pass through the membrane;

an output tap of the retentate of the low chamber, the output tap being configured to adjust the flow rate emptying out from the low chamber through the second side; and an output tap of the permeate of the high chamber extending through the top of the filtration device, the output tap of the permeate being subjected to negative pressure, the negative pressure drawing fluid with particles small enough to pass through the membrane from the low chamber, through the membrane and into the high chamber, wherein the base comprises ribs that form a set of baffles so as to provide circulation of the complex fluid composition to assist in limiting the clogging of the membrane with particles too large to pass through the membrane.

2. The device for the filtration of a complex fluid composition according to claim 1, wherein the base ribs are oriented perpendicularly to the input tap.

3. The device for the filtration of a complex fluid composition according to claim 2, wherein the top comprises ribs that form a set of baffles.

4. The device for the filtration of a complex fluid composition according to claim 3, wherein the base ribs and the top ribs are opposite so as to immobilize the membrane.

5. The device for the filtration of a complex fluid composition according to claim 1, wherein the base comprises a flange that is configured to accommodate an annular wall of the top so as to ensure the peripheral immobilization of the membrane.

6. The device for the filtration of a complex fluid composition according to claim 1, wherein the base comprises a flange that is configured to accommodate an annular wall of the top so as to ensure the peripheral immobilization of the membrane.

7. The device for the filtration of a complex fluid composition according to claim 6, wherein the base ribs are oriented perpendicularly to the input tap.

8. The device for the filtration of a complex fluid composition according to claim 1, wherein the base ribs are oriented perpendicularly with respect to the membrane.

9. The device for the filtration of a complex fluid composition according to claim 8, wherein the base ribs extend from the bottom of the base to the membrane.

10. The device for the filtration of a complex fluid composition according to claim 1, wherein the top ribs are oriented perpendicularly with respect to the membrane.

11. The device for the filtration of a complex fluid composition according to claim 10, wherein the top ribs extend from the bottom of the top to the membrane.

12. The device for the filtration of a complex fluid composition according to claim 1, wherein the base ribs form a first set of baffles extending to one side of the membrane, and the top comprises a second set of ribs that form a second set of baffles extending to an opposite side of the membrane, one of the base ribs extending to the one side of the membrane at a position corresponding to a position of one of the top ribs extending to the opposite side of the membrane.

13. A device for the filtration of a complex fluid composition, comprising:

a base with a bottom extending in a first direction;

a top arranged over the base;

a first side extending between the base and the top;

a second side opposite the first side extending between the base and the top;

a membrane that is arranged between said base and said top so as to define a low chamber and a high chamber, the first and second sides being disposed with the low and high chambers therebetween;

an input tap of the complex fluid composition to be filtered that empties into the low chamber through the first side, the low chamber being disposed below the high chamber with respect to a direction of flow of the complex fluid composition from the low chamber to the high chamber, the direction of flow from the low chamber to the high chamber being transverse to the first direction and opposite a direction of gravity so that gravity assists in limiting the clogging of the membrane with particles too large to pass through the membrane;

an output tap of the retentate of the low chamber, the output tap being configured to adjust the flow rate emptying out from the low chamber through the second side; and an output tap of the permeate of the high chamber extending from the top of the filtration device, passing through the bottom of the base in an airtight manner, passing through the membrane in an airtight manner, and comprising perforations in the part of the output tap of the permeate located within the high chamber so as to allow the permeate to pass, the output tap of the permeate being subjected to negative pressure, the negative pressure drawing fluid with particles small enough to pass through the membrane from the low chamber, through the membrane and into the high chamber, wherein the base comprises ribs that form a set of baffles so as to provide circulation of the complex fluid composition to assist in limiting the clogging of the membrane with particles too large to pass through the membrane.

14. The device for the filtration of a complex fluid composition according to claim 13, wherein the base ribs are oriented perpendicularly to the input tap.

* * * * *